United States Patent
Kumar et al.

(10) Patent No.: US 8,952,170 B2
(45) Date of Patent: Feb. 10, 2015

(54) CATALYTIC PROCESS FOR PRODUCTION OF PYRIDINE CARBOXYLIC ACID AMIDES

(75) Inventors: Mahendra Kumar, Bhartiyagram (IN); Shailendra Kumar Singh, Bhartiyagram (IN); Ashutosh Agarwal, Noida (IN)

(73) Assignee: Jubilant Life Sciences, Ltd., Uttar Pradesh (IN)

( * ) Notice: Subject to any disclaimer, the term of this patent is extended or adjusted under 35 U.S.C. 154(b) by 0 days.

(21) Appl. No.: 14/112,018

(22) PCT Filed: Apr. 14, 2012

(86) PCT No.: PCT/IB2012/000745
§ 371 (c)(1),
(2), (4) Date: Dec. 3, 2013

(87) PCT Pub. No.: WO2012/143771
PCT Pub. Date: Oct. 26, 2012

(65) Prior Publication Data
US 2014/0081029 A1 Mar. 20, 2014

(30) Foreign Application Priority Data
Apr. 18, 2011 (IN) .................... 1137/DEL/2011

(51) Int. Cl.
*C07D 213/82* (2006.01)
*B01J 23/34* (2006.01)
*C07D 213/81* (2006.01)
*B01J 23/86* (2006.01)

(52) U.S. Cl.
CPC ............ *C07D 213/82* (2013.01); *C07D 213/81* (2013.01); *B01J 23/34* (2013.01); *B01J 23/864* (2013.01); *B01J 23/866* (2013.01)
USPC ............................ 546/317; 546/323; 502/100

(58) Field of Classification Search
None
See application file for complete search history.

(56) References Cited

FOREIGN PATENT DOCUMENTS

CN 1807409 A 7/2006
CN 101851194 A 10/2010

OTHER PUBLICATIONS

Breno, Kerry L., et al., "Organometallic Chemistry in Aqueous Solution. Hydration of Nitriles to Amides Catalyzed by a Water-Soluble Molybdocene, (MeCp)2Mo(OH)(H2O)+," Organometallics, 2003, 22, pp. 1203-1211, ISSN: 0276-7333, see p. 1206.
Magdalena, Kolodziejska-Huben et al., "Preparation of 18 O-labeled nicotinamide," Journal of Labelled Compounds & Radiopharmaceuticals, 2002, 45, pp. 1005-1010, ISSN: 0362-4803, Figures 1, 3-4.
ISA/CN, "International Search Report and Written Opinion for International Application No. PCT/IB2012/000745," Sep. 13, 2012, 9 pages.

*Primary Examiner* — Zinna Northington Davis
(74) *Attorney, Agent, or Firm* — Fish & Tsang, LLP

(57) ABSTRACT

An improved catalytic process for the production of pyridine carboxylic acid amides, by catalytic hydration reaction of pyridine nitriles with solid heterogeneous catalyst wherein the process involve effective utilization and recycling of the catalytic components, and reactants.

16 Claims, No Drawings

CATALYTIC PROCESS FOR PRODUCTION OF PYRIDINE CARBOXYLIC ACID AMIDES

FIELD OF THE INVENTION

This invention, in general, relates to an improved catalytic process for the production of pyridine carboxylic acid amides on commercial scale. More particularly, the present invention provides an eco-friendly process for large-scale industrial production of pyridine carboxylic acid amide compounds, analogs, substituted forms, derivatives or the pharmaceutically acceptable salts, esters, prodrugs, solvates and hydrates thereof, with improved yield, selectivity and purity by catalytic hydration reaction of pyridine nitriles with solid heterogeneous catalyst wherein the process involve effective utilization and recycling of the catalytic components and reactants.

BACKGROUND OF THE INVENTION

Several processes are reported for the hydrolysis of pyridine nitriles to amides. The conversion of nitriles to amides has been achieved by both chemical and biological means.

Generally, it is known that microorganisms containing nitrile hydratase convert nitriles to the corresponding amides. European patent No. 188316 describes a process for the preparation of nicotinamide starting from 3-cyanopyridine using microorganisms of the genus *Rhodococcus, Arthrobacter* or *Microbacterium*.

European patent No. 307926 describes the conversion of 3-cyanopyridine to nicotinamide by means of microorganisms of the species *Rhodococcus rhodochrous* J1.

European patent No. 362829 reported the addition of urea or a urea derivative to the culturing medium as an inducer, in order to increase the specific activity of the microorganisms containing nitrile hydratase.

U.S. Pat. No. 5,827,699 discloses a process for the preparation of aromatic amides starting from the corresponding nitriles by means of microorganisms of the species *Rhodococcus rhodochrous* M33.

The disadvantage of most of these biological processes is that most of these micro-organisms have only a low activity for the conversion of cyanopyridine to pyridine amide. Further, some of the microorganisms are colored and accordingly a discoloration of the product takes place. In addition, these microorganisms have low heat stability and are inhibited, for example, by the substrate nitrile pyridine.

Several chemical processes are also reported for the preparation of pyridine amide compounds. Japanese Patent No. 93-206579 and European Patent No. 85-306670 describes the use of a modified Raney Nickel catalyst for the hydrolysis reaction.

U.S. Pat. No. 2,471,518; U.S. Pat. No. 4,721,709 and U.S. Pat. No. 4,314,064 discloses the hydrolysis of 3-cyanopyridine in the presence of sodium hydroxide. Rossa and Smith in Chemical Engineering Science, 1975, 35, 330 reported the use of magnesium oxide catalyst for the hydration reaction.

However, these reported processes have several disadvantages, for example, low yield, high reaction temperature and high alkali concentration. Moreover, high amount of nicotinic acid is also produced along with nicotinamide in these processes.

British Patent No. 1133013 describes the catalytic hydration of nitriles by manganese dioxide, prepared by the redox method using potassium permanganate and manganese sulphate in an alkaline medium. The hydration of 3-cyanopyridine/4-cyanopyridine is conducted using a catalyst in the mole ratio of 2.16:1. The yield reported is only 79.28 mole %. The main drawbacks of the process are that the yield is less, it is not eco-friendly and the amount of catalyst per mole of the feed for conversion is quite high.

U.S. Pat. No. 4,008,241 discloses the production of nicotinamide from 3-cyanopyridine by aqueous ammonia solution. The reaction temperature is 90-150° C., the reaction time is 4-8 hours and the ammonia concentration is 3-8 molar. The maximum conversion of 3-cyanopyridine is about 70%. However, this process involves multi-step separation of product from hydrolysis effluent which contains nicotinamide, ammonia, unconverted 3-cyanopyridine and ammonium nicotinate thereby making it less cost effective and tedious to get the pure product.

Sakai et al. in Bull. Chem. Soc., Japan, 1967, 40, 1660 have reported preparation of nicotinamide and isonicotinamide using nickel oxide as a catalyst. However, the catalytic activity as well as yield is low.

Indian patent No. 194989; U.S. Pat. Nos. 7,345,176 and 7,455,827 also discloses a process for the preparation of manganese dioxide catalyst useful for the preparation of nicotinamide and isonicotinamide. Manganese dioxide catalyst is prepared by redox method using potassium permanganate and manganese chloride in neutral medium to obtain the reaction mixture and then continuously stirring the obtained reaction mixture, filtering and drying to obtain the manganese dioxide catalyst. The yield of nicotinamide reported is 91.8 mole % and selectivity is 100%. However, when these processes were conducted in laboratory, no reproducible results were obtained. Moreover, no mention of niacin formation at reaction stage or at final product, no recycling during catalyst preparation or during amide preparation makes the process economically unattractive. Further, concentration of 3-cyanpoyridine in water is very low resulting into low productivity of niacinamide.

Chinese patent No. 101851194 discloses a method for the preparation of niacinamide with high yield and selectivity by dissolving 3-cyanopyridine in ethyl alcohol, water and catalyst at 80-100° C. in 6-10 h reaction time to give 99.7% niacinamide, 0.3% nicotinic acid. However, the main draw backs of this invention is the use of higher amount of catalyst (20% w/w of 3-cyanopyridine); concentration of 3-cyanopyridine in solvent is only 25% which leads to lower productivity.

Thus, the processes disclosed in the prior art have several disadvantages to be used for the commercial manufacturing of pyridine carboxylic acid amides. For example, most of the processes results in the formation of pyridine carboxylic acid, removal of which is conventional and cumbersome resulting into low recovery of product. The prior art processes involves multi-step, capital intensive purification process, which also results in generation of large amount of effluents, consequently making the process costly and uneconomical. Further, the processes can be used for producing small batches of the desired products in low yield and at higher costs, hence making the processes unsuitable for large-scale production.

The catalysts reported in the prior art, have number of serious drawbacks. These catalysts reported in the prior art quickly lose activity making it necessary to carry out frequent reactivation or use of new catalyst. In some of the prior art though the overall yield is increased but the product obtained is impure thereby requiring several steps for extraction and tedious isolation to obtain the desired products.

Thus, there is a need to develop a process for the production of pyridine carboxylic acid amides and catalyst for the process at industrial scale, which can improve the yield, selectivity, quality and minimize effluent generation to greater extent.

Therefore the present invention provides a solution to the aforesaid problems of the prior arts overcoming the above drawbacks and disadvantages by employing an improved catalyst and a cost effective and eco-friendly process for the industrial scale production of pyridine carboxylic acid amides.

SUMMARY OF THE INVENTION

It is an embodiment of the present invention to provide an improved large scale industrial process for producing pyridine carboxylic acid amide compounds, analogs, substituted forms, derivatives, or the pharmaceutically acceptable salts, esters, prodrugs, solvates and hydrates thereof wherein the process enables production of the compounds at industrial scale with minimal discharge.

It is another embodiment of the present invention to provide a cost effective and commercially viable process for producing pyridine carboxylic acid amide compounds, analogs, substituted forms, derivatives, or the pharmaceutically acceptable salts, esters, prodrugs, solvates and hydrates thereof, wherein the process provides pure product.

The present invention is based on green chemistry technology. It is an embodiment of the present invention to provide a cost effective, commercially viable and eco-friendly process for producing pyridine carboxylic acid amide compounds, analogs, substituted forms, derivatives, or the pharmaceutically acceptable salts, esters, amides, prodrugs, solvates and hydrates thereof wherein the process involves effective designing and managing of process which includes recovering, recycling and reutilizing of the mother liquor, catalyst, water, starting material, spent catalyst and by product.

The above and other embodiments of the present invention are further attained and supported by the following embodiments described herein. However, the scope of the invention is not restricted to the described embodiments herein after.

In accordance with one embodiment of the present invention, there is provided an improved industrial process for producing pyridine carboxylic acid amide compounds analogs, substituted forms, derivatives, or the pharmaceutically acceptable salts, esters, prodrugs, solvates and hydrates thereof, wherein the process comprising a catalytic hydrolysis of pyridine nitrile compound with water in the presence of a solid heterogeneous catalyst and optionally in alcohol, wherein the catalyst, water and other reactant materials are completely reused and wherein the catalyst, when deactivated is regenerated and reused in the process.

In accordance with one other embodiment of the present invention, there is provided an improved industrial process for producing pyridine carboxylic acid amide compounds, analogs, substituted forms, derivatives, or the pharmaceutically acceptable salts, esters, prodrugs, solvates and hydrates thereof, wherein the deactivated catalyst is regenerated by a process comprising reacting the deactivated catalyst with acid to obtain aqueous solution of metal salt and converting the resultant to active catalyst, wherein utilizing the byproduct, if generated during the regeneration process for other processes.

In accordance with one other embodiment of the present invention, there is provided a large scale industrial process for producing pyridine carboxylic acid amide compounds, analogs, substituted forms, derivatives, or the pharmaceutically acceptable salts, esters, prodrugs, solvates and hydrates thereof and catalyst for the process, wherein the water used in the processes is demineralized water having pH of 7.3-8.0.

In accordance with another embodiment of the present invention, the catalyst is oxides, hydroxides, carbonates, bicarbonates, nitrates, sulphates, halides, acetates, chelates, complexes and nanoparticles of metals from the group IIA, IIIB, IVB, VB, VIB, VIIB, VIIIB, IB, IIB, IIIA and IVA of the periodic table or mixtures thereof.

In accordance with one other embodiment of the present invention, there is provided an improved industrial process for producing pyridine carboxylic acid amide compounds, analogs, substituted forms, derivatives, or the pharmaceutically acceptable salts, esters, prodrugs, solvates and hydrates thereof, wherein the nitrile is 3-cyanopyridine and the pyridine carboxylic acid amide is niacinamide.

In accordance with yet another embodiment of the present invention, there is provided an improved industrial process for producing pyridine carboxylic acid amide compounds, analogs, substituted forms, derivatives, or the pharmaceutically acceptable salts, esters, prodrugs, solvates and hydrates thereof, wherein the nitrile is 4-cyanopyridine and the pyridine carboxylic acid amide is isoniacinamide.

In accordance with yet another embodiment of the present invention, there is provided an improved industrial process for producing pyridine carboxylic acid amide compounds, analogs, substituted forms, derivatives, or the pharmaceutically acceptable salts, esters, prodrugs, solvates and hydrates thereof, wherein the nitrile is 2-cyanopyridine and the pyridine carboxylic acid amide is picolinamide.

In accordance with yet another embodiment of the present invention, there is provided a process for preparing a catalyst for producing pyridine carboxylic acid amide compounds, analogs, substituted forms, derivatives, or the pharmaceutically acceptable salts, esters, prodrugs, solvates and hydrates thereof, wherein the process comprises of reacting an oxidizing and reducing agent in the presence of water to obtain a precipitate reaction mass, wherein at least one oxidizing or the reducing agent comprises at least one water soluble salt of metal; filtering the precipitate reaction mass, washing the obtained precipitate with water, drying the precipitate to obtain catalyst and reusing the mother liquor obtained in the preparation of catalyst.

In accordance with yet another embodiment of the present invention, the process for preparing a catalyst for producing pyridine carboxylic acid amide compounds, analogs, substituted forms, derivatives, or the pharmaceutically acceptable salts, esters, prodrugs, solvates and hydrates thereof, wherein the average particle size of the catalyst is in the range of 1 to 100μ and the specific surface area is in the range of 10 $m^2/g$ to 300 $m^2/g$.

Other aspects will be set forth in the description which follows, and in part will be apparent from the description or may be learnt by the practice of the invention.

DETAILED DESCRIPTION OF THE INVENTION

While this specification concludes with claims and appreciating that the content of the entire disclosure contains features of particular embodiments of the invention, it is anticipated that the invention can be more readily understood through reading the following detailed description of the invention and study of the included examples.

This invention, in general, relates to an improved catalytic process for the production of pyridine carboxylic acid amides on commercial scale. More particularly, the present invention provides an eco-friendly process for large-scale industrial production of pyridine carboxylic acid amide compounds, analogs, substituted forms, derivatives or the pharmaceutically acceptable salts, esters, prodrugs, solvates and hydrates thereof, with improved yield, selectivity and purity by catalytic hydration reaction of pyridine nitriles with solid heterogeneous catalyst wherein the process involve effective utilization and recycling of the catalytic components, reactants and starting materials.

Niacinamide is one of the water-soluble B-complex vitamins. Along with niacin it forms Vitamin B3 which is an important nutrient for brain health. It is a key nutrient for mitochondria which are the powerhouse for brain cells. Niacinamide supplements are very effective in preventing type I diabetes.

Thus, due to their important role, the quality of niacinamide and other products of the present invention are significant. The need is to develop a commercially viable, environmental friendly process for the production of pyridine carboxylic acid amide compounds, analogs, substituted forms, derivatives, or the pharmaceutically acceptable salts, esters, prodrugs, solvates and hydrates thereof, at industrial scale, which can improve yield, selectivity and quality of desired compounds and minimize the effluent generation to greater extent. The present invention provides a solution to this and aforesaid problems of the prior arts, employing an improved catalyst and process for producing pyridine carboxylic acid amide of required specifications.

The disclosed embodiment of the present invention provide an eco-friendly and cost effective process following the green chemistry principles, for producing pyridine carboxylic acid amide compounds, analogs, substituted forms, derivatives, or the pharmaceutically acceptable salts, esters, prodrugs, solvates and hydrates thereof, wherein the process involves effective recovering and recycling of all the reagents, unreacted reactants, catalyst and other materials used or formed in the process thereby minimizing environmental hazards and cost involve in waste disposal as also consumption of reactants, reagents, catalyst required for the reaction. Also, the high purity of the catalyst of the present invention reduces the consumption and frequent deactivation of catalyst.

The disclosed embodiment of the present invention deals with an improved large scale industrial process for producing pyridine carboxylic acid amide compounds analogs, substituted forms, derivatives, or the pharmaceutically acceptable salts, esters, prodrugs, solvates and hydrates thereof, wherein the process comprises of hydrolyzing a pyridine nitrile compound in the presence of solid heterogeneous catalyst, separating the obtained hydrolysed pyridine carboxylic acid amide, reusing the catalyst obtained for the hydrolysis step and reusing the water and other reactant materials obtained for the hydrolysis step.

The process according to the present invention, for producing a pyridine carboxylic acid amide compounds, analogs, substituted forms, derivatives, or the pharmaceutically acceptable salts, esters, prodrugs, solvates and hydrates thereof comprising:
  a. hydrolyzing pyridine nitrile compound with water in the presence of a solid heterogeneous catalyst, optionally in alcohol,
  b. separating the pyridine carboxylic acid amide reaction mass from catalyst;
  c. recycling the catalyst obtained in separating step (b), in the hydrolysis step (a) of the nitrile compound;
  d. separating pyridine carboxylic acid amide from the solution obtained in step (b);
  e. drying to obtain pyridine carboxylic acid amide and
  f. recovering and recycling the water and other reactant materials obtained in step (d), in the hydrolysis step of the nitrile compound.

According to the process of the present invention, the solid heterogeneous catalyst used is selected from the group comprising of oxides, hydroxides, carbonates, bicarbonates, nitrates, sulphates, halides, acetates, chelates, complexes and nanoparticles of metals from the periodic table, preferably from group IIA, IIIB, IVB, VB, VIB, VIIB, VIIIB, IB, IIB, IIIA and IVA of the periodic table and mixtures thereof.

The catalyst is selected from the group comprising of oxides, hydroxides, carbonates, bicarbonates, nitrates, sulphates, halides, acetates, chelates, complexes, nanoparticles of manganese, cobalt, nickel, lead, copper, aluminium, rhuthenium, silver, zinc, cadmium, iron, molybdenum, chromium, magnesium, vanadium, zirconium, indium, and mixtures thereof, preferably of nickel, manganese, copper, aluminium, chromium, cobalt, lead, cadmium, zinc, iron, magnesium and mixtures thereof.

According to the process of the present invention, the water used in the processes is demineralized water having pH in the range of 7.3-8.0 preferably 7.5-8.0.

According to the process of the present invention, the alcohol used herein is lower alcohol and mixtures thereof. The lower alcohol, used herein is selected from the group comprising of methanol, ethanol, n-propanol, isopropanol, butanol and mixtures thereof.

The reaction is carried out for a time period of about 3-20 hrs, preferably about 6-15 hrs, in the temperature range of about 60 to 110° C., preferably at about 75-95° C.

According to the process of the present invention, the average particle size of the catalyst is in the range of 1 to 100μ and the specific surface area is in the range of 10 m$^2$/g to 300 m$^2$/g, preferably 50 m$^2$/g to 250 m$^2$/g.

According to the process of the present invention, the ratio of pyridine nitrile to catalyst is in the range of about 1:0.05 to 0.2, preferably in the range of about 1:0.06 to 0.15.

According to the process of the present invention, the other reactant materials obtained in step (d) includes unreacted pyridine nitrile and alcohol.

According to the process of the present invention, the other reactant materials are reused up to 99.5%.

According to the process, the pyridine carboxylic acid amides obtained are dried by spray drying or other commercially practiced drying processes.

According to the process of the present invention, the recycling step (c) of catalyst comprises of washing catalyst with water and utilizing the obtained product as a catalyst for the hydrolysis of nitrile compound, wherein the water used in the processes is demineralized water having pH of 7.3-8.0 preferably 7.5-8.0.

According to the process of the present invention, the process further comprises a step of reutilizing spent or deactivated catalyst obtained after recycles, wherein the process comprises of reacting the deactivated catalyst with acid to obtain aqueous solution of metal salt and converting the resultant to active catalyst, wherein the byproduct, if generated during the regeneration process is utilized for other processes.

According to the process the nitrile is 3-cyanopyridine and the pyridine carboxylic acid amide is niacinamide, wherein the niacinamide is produced with greater than 99.5% purity having niacin content less than 0.25%.

According to the process the nitrile is 4-cyanopyridine and the pyridine carboxylic acid amide is isoniacinamide.

According to the process the nitrile is 2-cyanopyridine and the pyridine carboxylic acid amide is picolinamide.

According to the process, the hydrolysis reaction of the present invention can be performed continuously and batchwise.

According to the another aspect of the present invention, there is provided a process for the preparation of catalyst useful for producing a pyridine carboxylic acid amide compounds, analogs, substituted forms, derivatives, or the pharmaceutically acceptable salts, esters, prodrugs, solvates and hydrates thereof, wherein the process comprising;
- a) reacting an oxidizing and reducing agent in the presence of water to obtain a precipitate reaction mass, wherein at least one oxidizing or the reducing agent comprises at least one water soluble salt of metal;
- b) filtering the precipitate reaction mass;
- c) washing the obtained precipitate with water;
- d) drying the precipitate to obtain catalyst and
- e) reusing mother liquor obtained in step (c) in the preparation of catalyst.

The redox reaction is carried out in the temperature range of about 25 to 30° C.

According to the process for producing the catalyst, the drying in step (d) is carried out in the temperature range of about 90-150° C., preferably at about 110-130° C. The assay of the catalyst obtained by both the process of the present invention is more than 90%.

The form in particular of the catalyst is not limited to particles, granules, powder, pellets, spheres, etc. to be utilized in any engineering practice viz. fixed bed, fluidized bed, stirred tank reactor, etc. for the hydration reaction of nitrile in a batch type or a continuous type reactor.

According to the process of the present invention, the average particle size of the catalyst is in the range of 1 to 100μ and the specific surface area of the catalyst is in the range of 10 $m^2/g$ to 300 $m^2/g$, preferably 50 $m^2/g$ to 250 $m^2/g$.

According to the process for producing the catalyst, the by product, if generated during the preparation of catalyst is utilized for other processes.

According to the process for producing the catalyst, wherein the catalyst comprises oxides, hydroxides, carbonates, bicarbonates, nitrates, sulphates, halides, acetates, chelates, complexes, nanoparticles of nickel, manganese, copper, aluminium, chromium, cobalt, lead, cadmium, zinc, iron, magnesium and mixtures thereof.

The present invention is further illustrated below with reference to the following examples without intending to limit the scope of the invention in any manner.

EXAMPLE 1

Catalyst Preparation

The aqueous solution of manganese chloride tetra hydrate (134 g) and 600 g de-mineralized water was added drop wise to an aqueous solution of potassium permanganate (70 g) in 1350 g de-mineralized water (pH 7.5) at 25-30° C. with continuous stiffing. The resulting reaction mass was left standing for 8-10 hours. The precipitate was filtered and washed with de-mineralized water. The mother liquor was collected. The wet catalyst (320 g) was dried at 110-120° C. for 4-5 hours to get 103 g manganese dioxide having assay 91% having surface area 168 $m^2/g$ and particle size distribution <25μ.

EXAMPLE 2

Catalyst Preparation

The chromium nitrate, 9-hydrate (20 g) and nickel nitrate hexa hydrate (3 g) were added in 35 g de-mineralized water (pH 7.5) at 25-30° C. with continuous stiffing. The resulting reaction mass was left standing for 8-10 hours. The green color precipitate was filtered and washed with de-mineralized water. The mother liquor was collected. The wet catalyst was dried at 120° C. overnight to get chromium oxide-nickel oxide catalyst.

EXAMPLE 3

Catalyst Preparation

The aqueous solution of cobaltous nitrate hexahydrate (35 g) and 85 g de-mineralized water was added drop wise to an aqueous solution of chromium nitrate, 9-hydrate (70 g) in 85 g de-mineralized water (pH 7.5) at 25-30° C. with continuous stirring.

The resulting reaction mass was left standing for 8-10 hours. The brown precipitate was filtered and washed with de-mineralized water. The mother liquor was collected. The wet catalyst was dried at 120° C. overnight to get 18 g of chromium oxide-cobalt oxide catalyst.

In accordance with the procedure of Example 1-3, the other catalysts were also prepared.

EXAMPLE 4

Recycle of Aqueous Mother Liquor

The aqueous solution of manganese chloride tetra hydrate (134 g) in 600 g mother liquor obtained in Example 1 was added drop wise to aqueous solution of potassium permanganate (70 g) in 1350 g mother liquor obtained in example 1 at 25-30° C. with continuous stirring. The resulting reaction was left standing for 8-10 hours. The precipitate was filtered and washed with de-mineralized water. The mother liquor was collected. The wet catalyst was dried at 110-120° C. for 4-5 hours to get 100 g catalyst having assay 91.5%. Surface area: 165 $m^2/g$. The mother liquor was recycled up to 5th recycle to reduce effluent generation.

EXAMPLE 5

Catalytic Hydration of 3-Cyanopyridine to Niacinamide

In a four neck round bottom flask fitted with thermowell, agitator and reflux condenser, 3-cyanopyridine (500 g), de-mineralized water (560 g; pH 7.5), ethyl alcohol (56 g) and 40 g of fresh catalyst prepared in Example 1 were charged. The mixture was heated up to 85-90° C. for 4-6 hrs. The completion of reaction was monitored by HPLC. After the completion of reaction the crude product was cooled to 50-60° C. and filtered to separate niacinamide from the catalyst bed. The catalyst bed was washed with de-mineralized water to make catalyst free from hydrolyzed mass of 3-cyanopyridine. The wet catalyst obtained was recycled back for next batch of hydrolysis. The colorless mother liquor was concentrated and dried to get 561.5 g niacinamide. Purity: 99.6% (w/w); niacin content<0.23%; Melting Point: 128-131° C. The water layer recovered containing 3-cyanopyridine and alcohol was recycled back for next hydrolysis batch.

EXAMPLE 6

Recycle of Catalyst, Water and Alcohol

In a four neck round bottom flask fitted with thermo well, agitator and reflux condenser, 3-cyanopyridine (500 g), recovered water layer (560 g; pH 7.5) containing 3-cyanopyridine and alcohol in Example 5, 36 g of fresh ethyl alcohol and recovered catalyst in Example 5 and fresh catalyst were charged. The mixture was heated up to 85-90° C. for 8-12 h. The completion of reaction was monitored by HPLC. After the completion of reaction the crude product was cooled to 50-60° C. and filtered to separate niacinamide from the catalyst bed. The catalyst bed was washed with de-mineralized water to make catalyst free from hydrolyzed mass of 3-cyanopyridine. The wet catalyst was recycled back for next batch of hydrolysis. The colorless mother liquor was concentrated and dried to get 565.8 g niacinamide. Purity: 99.5% (w/w); niacin content <0.25%. The water layer recovered containing 3-cyanopyridine and alcohol was recycled back for next hydrolysis batch.

The catalyst, when deactivated, was converted into manganese salt, which was again used in preparation of fresh catalyst.

EXAMPLE 7

Regeneration of Spent Catalyst 360 g Hydrochloric acid (30%) was added slowly into mixture of 72 g spent catalyst and 100 g de-mineralized water at ambient temperature. After addition, the mixture was heated up to 70° C. for 5 to 6 h to get 504 g of aqueous solution of manganese chloride. Chlorine liberated during reaction was scrubbed in 730 g (10% NaOH) solution to obtain hypo solution (780 g, % NaOCl=7.5%, % NaOH=1.0%), which was used as bleaching agent. Aqueous solution of manganese chloride obtained was used in the preparation of catalyst as per Example 1.

EXAMPLE 8

Catalytic Hydration of 4-Cyanopyridine to Isoniacinamide

In a four neck round bottom flask fitted with thermo well, agitator and reflux condenser, 4-cyanopyridine (100 g), de-mineralized water (150 g), isopropyl alcohol (10 g) and chromium oxide-cobalt oxide catalyst (1 g) prepared in Example 3 were charged. The mixture was heated up to 85-90° C. for 4-6 h. The completion of reaction was monitored by HPLC. After the completion of reaction the crude product was cooled and filtered to separate isoniacinamide from the catalyst bed. The catalyst bed was washed with de-mineralized water to make catalyst free from hydrolyzed mass of 4-cyanopyridine. The wet catalyst was recycled back for next batch of hydrolysis. The colorless mother liquor was concentrated and dried to get 110 g isoniacinamide. Purity: 99.4% (w/w); isonicotinic acid <0.39%. The recovered water layer containing 4-cyanopyridine and alcohol was recycled back for next hydrolysis batch.

EXAMPLE 9

Catalytic Hydration of 2-Cyanopyridine to Picolinamide

In a four neck round bottom flask fitted with thermo well, agitator and reflux condenser, 2-cyanopyridine (100 g), de-mineralized water (150 g) isopropyl alcohol (10 g) and chromium oxide-nickel oxide catalyst (1 g) prepared in Example 2 is charged. The mixture is heated up to 85-90° C. for 4-6 h. The completion of reaction is monitored by HPLC. After the completion of reaction the crude product is cooled and filtered to separate picolinamide from the catalyst bed. The catalyst bed is washed with de-mineralized water to make catalyst free from hydrolyzed mass of 2-cyanopyridine. The wet catalyst is recycled back for next batch of hydrolysis. The colorless mother liquor is concentrated and dried to get pure picolinamide. The recovered water layer containing 2-cyanopyridine and alcohol is recycled back for next hydrolysis batch.

While this invention has been described in detail with reference to certain preferred embodiments, it should be appreciated that the present invention is not limited to those preferred embodiments rather, in view of the present disclosure, which describes the current best mode for practicing the invention, many modifications and variations, would present themselves to those skilled in the art without departing from the scope and spirit of this invention. This invention is susceptible to considerable variation in its practice within the spirit and scope of the appended claims. All references recited herein are incorporated herein by specific reference in their entirety.

We claim:

1. A process for producing pyridine carboxylic acid amide compounds, analogs, substituted forms, derivatives, or pharmaceutically acceptable salts, esters, solvates and hydrates thereof, the process comprising:
   a catalytic hydrolysis of pyridine nitrile compound with water in the presence of a solid heterogeneous catalyst, optionally in alcohol,
   wherein the catalyst, water and other reactant materials are reused and wherein the catalyst, when deactivated is regenerated and reused in the process,
   wherein the water used is demineralized water having pH in the range of 7.3-8.0.

2. The process according to claim 1, wherein the catalyst is selected from the group comprising oxides, hydroxides, carbonates, bicarbonates, nitrates, sulphates, halides, acetates, chelates, complexes, nanoparticles of metals from group IIA, IIIB, IVB, VB, VIB, VIIB, VIIIB, IB, IIB, IIIA and IVA of the periodic table and mixtures thereof.

3. The process according to claim 1, wherein the catalyst is selected from the group comprising oxides, hydroxides, carbonates, bicarbonates, nitrates, sulphates, halides, acetates, chelates, complexes, nanoparticles of manganese, cobalt, nickel, lead, copper, aluminium, rhuthenium, silver, zinc, cadmium, iron, molybdenum, chromium, magnesium, vanadium, zirconium, indium and mixtures thereof.

4. The process according to claim 1, wherein the alcohol is selected from the group comprising of methanol, ethanol, n-propanol, isopropanol, butanol and mixtures thereof.

5. The process of claim 1, wherein the specific surface area of the catalyst is in the range of 10 m2/g to 300 m2/g.

6. The process of claim 1, wherein the average particle size of the catalyst is in the range of 1 to 100μ.

7. The process according to claim 1, wherein the other reactant materials include unreacted pyridine nitrile and alcohol.

8. The process according to claim 1, wherein the other reactant materials are reused up to 99.5%.

9. The process according to claim 1, wherein the deactivated catalyst is regenerated by a process comprising:
   reacting the deactivated catalyst with acid to obtain aqueous solution of metal salt; and
   converting the resultant of the reacting of the deactivated catalyst with acid in order to obtain an active catalyst, wherein the by-product, if generated during the process, is utilized in other processes.

10. The process according to claim 1, wherein the nitrile is 3-cyanopyridine and the pyridine carboxylic acid amide is niacinamide.

11. The process according to claim 1, wherein the nitrile is 4-cyanopyridine and the pyridine carboxylic acid amide is isoniacinamide.

12. The process according to claim 1, wherein the nitrile is 2-cyanopyridine and the pyridine carboxylic acid amide is picolinamide.

13. The process according to claim 1, wherein the process is used for preparing a catalyst for producing pyridine carboxylic acid amide compounds, analogs, substituted forms, derivatives, or pharmaceutically acceptable salts, esters, solvates and hydrates thereof, the process further comprising:
   a) reacting an oxidizing and reducing agent in the presence of water to obtain a precipitate reaction mass, wherein at least one oxidizing or the reducing agent comprises at least one water soluble salt of metal;
   b) filtering the precipitate reaction mass;
   c) washing the obtained precipitate with water;
   d) drying the precipitate to obtain catalyst; and
   e) reusing the mother liquor obtained in step (c) in the preparation of catalyst.

14. The process of claim 13, wherein the specific surface area of the catalyst is in the range of 10 $m^2/g$ to 300 $m^2/g$.

15. The process of claim 13, wherein the average particle size of the catalyst is in the range of 1 to 100μ.

16. The process according to claim 13, wherein the catalyst comprises oxides, hydroxides, carbonates, bicarbonates, nitrates, sulphates, halides, acetates, chelates, complexes, nanoparticles of nickel, manganese, copper, aluminium, chromium, cobalt, lead, cadmium, zinc, iron, magnesium and mixtures thereof.

* * * * *